(12) United States Patent
Vuligonda et al.

(10) Patent No.: US 6,388,105 B1
(45) Date of Patent: May 14, 2002

(54) BENZOFURAN, INDOLE OR BENZOTHIOPHENE 2,4-PENTADIENOIC ACID DERIVATIVES HAVING SELECTIVE ACTIVITY FOR RETINOID X (RXR) RECEPTORS

(75) Inventors: Vidyasagar Vuligonda, Irvine; Roshantha A. Chandraratna, Laguna Hills, both of CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/967,130

(22) Filed: Sep. 27, 2001

(51) Int. Cl.⁷ ............ C07D 307/79; C07D 333/54; C07D 209/08
(52) U.S. Cl. ............ 549/471; 546/277.4; 546/281.1; 546/284.1; 548/469; 549/58
(58) Field of Search ............ 549/471, 58; 546/277.4, 546/281.1, 284.1; 548/469

(56) References Cited

U.S. PATENT DOCUMENTS 6,147,224 A * 11/2000 Vuligonda et al. .......... 549/406

* cited by examiner

Primary Examiner—Bernard Dentz
(74) Attorney, Agent, or Firm—Gabor L. Szekeres; Robert J. Baran; Martin A. Voet

(57) ABSTRACT

Compounds of the formula

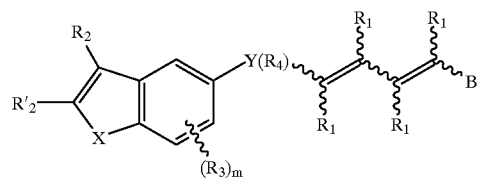

Where the variables are defined as in the specification, are selective agonists of RXR retinoid receptors.

30 Claims, No Drawings

BENZOFURAN, INDOLE OR BENZOTHIOPHENE 2,4-PENTADIENOIC ACID DERIVATIVES HAVING SELECTIVE ACTIVITY FOR RETINOID X (RXR) RECEPTORS

BACKGROUND OF THE INVENTION

1. Field of the Invention

The present invention relates to novel compounds having retinoid-like biological activity. More specifically, the present invention relates to benzofuranyl, indolyl or benzothienylcyclopropyl 2,4-pentadienoic acid derivatives and to benzofuranyl, indolyl or benzothienylaryl or heteroaryl 2,4-pentadienoic acid derivatives having selective activity for retinoid X (RXR) receptors.

2. Background Art

Compounds which have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system metaplasias, dysplasias, neoplasias, leukoplakias and papillomas of the mucous membranes and in the treatment of Kaposi's sarcoma. In addition, retinoid compounds can-be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil$^R$, diseases associated with the immune system, including use of the present compounds as immunosuppressants and immunostimulants, modulation of organ transplant rejection and facilitation of wound healing, including modulation of chelosis. Retinoid compounds have relatively recently been also discovered to be useful for treating type II non-insulin dependent diabetes mellitus (NIDDM).

It is now general knowledge in the art that two main types of retinoid receptors exist in mammals (and other organisms). The two main types or families of receptors are respectively designated the RARs and RXRs. Within each type there are subtypes; in the RAR family the subtypes are designated RAR$_\alpha$, RAR$_\beta$ and RAR$_\gamma$, in RXR the subtypes are: RXR$_\alpha$, RXR$_\beta$, and RXR$_\gamma$. It has also been established in the art that the distribution of the two main retinoid receptor types, and of the several sub-types is not uniform in the various tissues and organs of mammalian organisms. Moreover, it is generally accepted in the art that many unwanted side effects of retinoids are mediated by one or more of the RAR receptor subtypes. Accordingly; among compounds having agonist-like activity at retinoid receptors, specificity or selectivity for one of the main types or families, and even specificity or selectivity for one or more subtypes within a family of receptors, is considered a desirable pharmacological property. Some compounds bind to one or more RAR receptor subtypes, but do not trigger the response which is triggered by agonists of the same receptors. A compound that binds to a biological receptor but does not trigger an agonist-like response is usually termed an antagonist. Accordingly, the "effect" of compounds on retinoid receptors may fall in the range of having no effect at all, (inactive compound, neither agonist nor antagonist) or the compound may elicit an agonist-like response on all receptor subtypes (pan-agonist). As still another alternative a compound may be a partial agonist and/or partial antagonist of certain receptor subtypes if the compound binds to but does not activate certain receptor subtype or subtypes but elicits an agonist-like response in other receptor subtype or subtypes. A pan-antagonist is a compound that binds to all known retinoid receptors but does not elicit an agonist-like response in any of the receptors.

Recently a two-state model for certain receptors, including the above-mentioned retinoid receptors, have emerged. In this model, an equilibrium is postulated to exist between inactive receptors and spontaneously active receptors which are capable of coupling with a G protein in the absence of a ligand (agonist). In this model, so-called "inverse agonists" shift the equilibrium toward inactive receptors, thus bringing about an overall inhibitory effect. Neutral antagonists do not effect the receptor equilibrium but are capable of competing for the receptors with both agonists (ligands) and with inverse agonists. U.S. Pat. No. 5,877,207 titled "Synthesis and Use of Retinoid Compounds Having. Negative Hormone and/or Antagonist Activities" describes the foregoing two-state model and the use of retinoid antagonist and negative hormones in detail.

Among the scientific publications Dawson and William H. Okamura, *Chemistry and Biology of Synthetic Retinoids*, published by CRC Press Inc., 1990, pages 334–335, 354 and 324–356 is of special interest as an overview of the prior art on the subject.

The following is a list of United States and foreign patents and publications which disclose compounds having structural similarity to the compounds of the present invention, or disclose compounds having retinoid agonist, antagonist or inverse agonist like biological activity having a benzofuran, indole, benzothiophene or closely related moiety or a pentadienoic acid moiety: U.S. Pat. Nos. 6,172,115; 6,048,873; 6,034,110; 5,917,082; 6,093,838; 5,675,033; 6,147,224;

5,728,846; 5,324,840; 5,344,959; 5,466,861; WO 96/05165; WO 93/21162; EPO 0 098 591; Janusz et al. J. Med. Chem. 1998 41 1124–1137; Iida et al. Tetrahedron Letters 35, 1982 p 359–3594; Vuligonda et al. Biorg. Med. Chem. Lett. 6(2) 213—8, 1996.

SUMMARY OF THE INVENTION

The present invention relates to compounds of Formula 1

Formula 1

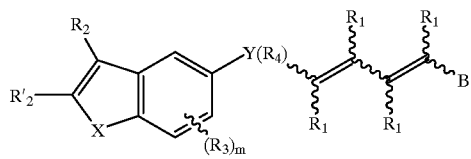

X is O, NR' or S where R' is alkyl of 1 to 6 carbons;

Y is a bivalent cyclopropyl radical optionally substituted with one or two $R_4$ groups, or Y is a bivalent aryl or 5 or 6 membered heteroaryl radical having 1 to 3 heteroatoms selected from N, S and O, said aryl or heteroaryl groups optionally substituted with 1 to 4 $R_4$ groups;

$R_1$ is independently H, alkyl of 1 to 6 carbons, or fluoroalkyl of 1 to 6 carbons;

$R_2$ is alkyl of 1 to 8 carbons, or fluoroalkyl of 1 to 8 carbons;

$R'_2$ is alkyl of 1 to 8 carbons, or fluoroalkyl of 1 to 8 carbons;

$R_3$ is hydrogen, alkyl of 1 to 6 carbons, fluoro substituted alkyl of 1 to 6 carbons, halogen, alkoxy of 1 to 8 carbons, or alkylthio of 1 to 6 carbons; $NO_2$, $NH_2$, $NHCO(C_1-C_6$ alkyl), $NHCO(C_1-C_6)$alkenyl, $NR_1H$ or $N(R_1)_2$, benzyloxy or $C_1-C_6$alkyl-substituted benzyloxy;

$R_4$ is H or alkyl of 1 to 6 carbons, or fluoro substituted alkyl of 1 to 6 carbons;

m is an integer having the values of 0 to 3, and

B is COOH or a pharmaceutically acceptable salt thereof, $COOR_8$, $COOCH_2COR_7$, $CONR_9R_{10}$, $-CH_2OH$, $CH_2OR_{11}$, $CH_2OCOR_{11}$, CHO, $CH(OR_{12})_2$, $CH(OR_{13}O)$, $-COR_7$, $CR_7(OR_{12})_2$, $CR_7(OR_{13}O)$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a group of 5 to 10 phenyl or lower alkylphenyl, $R_9$ and $R_{10}$ independently are hydrogen, an alkyl group of 1 to 10 carbons, or a cycloalkyl group of 5–10 carbons, or phenyl, hydroxyphenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

In a second aspect, this invention relates to the use of the compounds of Formula 1 for the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical antimicrobial, as skin anti-pigmentation agents and to treat and reverse the effects of age and photo damage to the skin. The compounds are also useful for the prevention and treatment of metabolic diseases such as type II diabetes and diabetes mellitus and for prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions and diseases associated with Human papilloma virus (HPV), including warts and genital warts, various inflammatory diseases such as pulmonary fibrosis,. ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil$^R$, diseases associated with the immune system, including use of the present compounds as immunosuppressants and immunostimulants, modulation of organ transplant rejection and facilitation of wound healing, including modulation of chelosis.

Generally speaking, the second aspect of the invention relates to the use of the novel compounds to prevent or treat diseases and conditions which are responsive to compounds that promote the expression of or bind to receptors belonging to the steroid or thyroid receptor superfamily.

This invention also relates to a pharmaceutical formulation comprising a compound of Formula 1 in admixture with a pharmaceutically acceptable excipient, said formulation being adapted for administration to a mammal, including a human being, to treat or alleviate the conditions which were described above as treatable by retinoids.

BIOLOGICAL ACTIVITY, MODES OF ADMINISTRATION

Assays of Retinoid-like Biological Activity

A classic measure of retinoic acid activity involves measuring the effects of retinoic acid on ornithine decarboxylase. The original work on the correlation between retinoic acid and a decrease in cell proliferation was done by Verma & Boutwell, Cancer Research, 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all cases for ODC activity increases are unknown, it is known that 12-0-tetradecanoylphorbol-13-acetate (TPA) induces ODC activity. Retinoic acid inhibits this induction of ODC activity by TPA. An assay essentially following the procedure set out in Cancer Research: 1662–1670,1975 may be used to demonstrate inhibition of TPA induction of ODC by compounds of this invention. "$IC_{60}$" is that concentration of the test compound which causes 60% inhibition in the ODC assay.

By analogy, "$IC_{80}$", for example, is that concentration of the test compound which causes 80% inhibition in the ODC assay.

Other assays described below, measure the ability of the compounds of the present invention to bind to, and/or activate various retinoid receptor subtypes. When in these assays a compound binds to a given receptor subtype and activates the transcription of a reporter gene through that subtype, then the compound is considered an agonist of that receptor subtype. Conversely, a compound is considered an antagonist of a given receptor subtype if in the below described co-tranfection assays the compound does not cause significant transcriptional activation of the receptor regulated reporter gene, but nevertheless binds to the receptor with a $K_d$ value of less than approximately 1 micromolar. In the below described assays the ability of the compounds to bind to $RAR_\alpha$, $RAR_\beta$, $RAR_\gamma$, $RXR_\alpha$, $RXR_\beta$ and $RX_\gamma$ receptors, and the ability or inability of the compounds to activate transcription of a reporter gene through these receptor subtypes can be tested. These assays are expected to demonstrate that the compounds of the present invention act as agonists of one or more of the above-described receptors. Because of the complex distribution of the different retinoid receptors in various organs of the mammalian body partial agonists may lend themselves to particularly useful therapeutic applications and may avoid serious side effects of conventional retinoid drugs.

As far as specific assays are concerned to demonstrate the activities of the compounds of the present invention, a chimeric receptor transactivation assay which tests for agonist-like activity in the $RAR_\alpha$, $RAR_\beta$, $RAR_\gamma$, $RXR_\alpha$ receptor subtypes, and which is based on work published by Feigner P. L. and Holm M (1989) Focus, 112 is described in detail in U.S. Pat. No. 5,455,265. The specification of U.S. Pat. No. 5,455,265 is hereby expressly incorporated by reference.

A holoreceptor transactivation assay and a ligand binding assay which measure the antagonist/agonist like activity of the compounds of the invention, or their ability to bind to the several retinoid receptor subtypes, respectively, are described in published PCT Application No. WO WO93/11755 (particularly on pages 30–33 and 37–41) published on Jun. 24, 1993, the specification of which is also incorporated herein by reference. A detailed experimental procedure for holoreceptor transactivations has been described by Heyman et al. Cell 68, 397–406, (1992); Allegretto et al. J. Biol. Chem. 268, 26625–26633, and Mangelsdorf et al. The Retinoids: Biology, Chemistry and Medicine, pp 319–349, Raven Press Ltd., New York, which are expressly incorporated herein by reference. The results obtained in this assay are expressed in $EC_{50}$ numbers, as they are also in the chimeric receptor transactivation assay. The results of ligand binding assay are expressed in $K_d$ numbers. (See Cheng et al. Biochemical Pharmacology Vol. 22 pp 3099–3108, expressly incorporated herein by reference.)

Still another transactivation assay, the "PGR assay" is described in the publication Klein et al. J. Biol. Chem. 271, 22692–22696 (1996) which is expressly incorporated herein by reference, and a detailed description is also provided below. The results of the PGR assay are also expressed in $EC_{50}$ numbers (nanomolar concentration).

RAR-PGR Holoreceptor Transactivation Assay

CV-1 cells ($4\times10^5$ cells/well) were transiently transfected with the luciferase reporter plasmid MTV-4(R5G)-Luc (0.7 ug/well) containing four copies of the R5G retinoid DNA response element along With the RXRα expression plasmid pRS-hRXRα (0.1 ug/well) and one of the RAR-P-GR expression plasmids (0.05 ug/well) in 12 well plates via calcium phosphate precipitation Chen et al. (1987) Mol. Cell. Biol. 7, 2745–2752 as described by Klein el al. in J. Biol. Chem. 271, 22692, referenced above. The three different RAR-P-GR expression plasmids, pRS-RARα-P-GR, pcDNA3-RARβ-P-GR-and pcDNA3-RARγ-P-GR, express RARα, RARβ and RARγ receptors, respectively, which contain modified DNA binding domains such that their "P-boxes" have been altered to that of the glucocorticoid receptor. These RAR-P-GR receptors bind to DNA as heterodimeric complexes with RXR. Specifically, the RAR-P-GR receptors bind retinoic acid response elements designated R5G, comprised of two RAR half sites (nucleotide sequence 5'-GGTTCA-3') separated by 5 base pairs in which the 3'-half site has been modified to that of a glucocorticoid receptor half site, 5'-AGAACA-3'. To allow for various in transfection efficiency a β-galactosidase expression plasmid (0.01 ug/well) was used as an internal control. Alternatively, the assay was performed in a 96-well microtiter plate format (5000 cells/well) in a manner which was identical to that described above except ⅕ of the amount of the DNA-calcium phosphate precipitant (20 µl instead of 100 µl) was applied to each well. Eighteen hours after introduction of the DNA precipitants, cells were rinsed with phosphate buffered saline (PBS) and fed with D-MEM (Gibco-BRL) containing 10% activated charcoal extracted fetal bovine serum (Gemini Bio-Products). Cells were treated for 18 hours with the compounds indicated in the figures. After rinsing with PBS cells were lysed with luciferase activity was measured as previously described in de Wet (1987) Mol. Cell. Biol. 7, 725–737. Luciferase values represent the mean±SEM of triplicate determinations normalized to β-galactosidase activity.

Table 1 discloses the activity of certain exemplary compounds of the invention in the above-described holoreceptor transactivation assay and a ligand binding assays. Particularly, the transactivation data pertaining to RAR receptors were obtained in the chimeric assay, and the data pertaining to transactivation of RXR receptors were obtained in the holoreceptor transactivation assay. In a chimeric receptor transactivation assay the compounds were essentially inactive in activating RARα, RARβ and RARγ receptors.

TABLE 1

| Compound # | | RXR | | |
|---|---|---|---|---|
| | | α | β | γ |
| 12 | $EC_{50}$ (nM) | 1.5 | 17 | 2.9 |
| | % Eff | 144 | 150 | 131 |
| | $K_d$ (nM) | 11 | 20 | 40 |
| 20 | $EC_{50}$ (nM) | 6 | 44 | 12 |
| | % Eff | 130 | 90 | 90 |
| | $K_d$ (nM) | 71 | 288 | 256 |
| 28 | $EC_{50}$ (nM) | 0.7 | 4.3 | 0.8 |
| | % Eff | 102 | 116 | 110 |
| | $K_d$ (nM) | 6.8 | 17 | 48 |
| 38 | $EC_{50}$ (nM) | 2.2 | 9.3 | 2.6 |
| | % Eff | 100 | 96 | 101 |
| | $K_d$ (nM) | 19.5 | 98 | >1000 |

As it can be seen from the foregoing assay results, the compounds of the invention are specific or selective agonists of RXR receptors.

Modes of Administration

The compounds of this invention may be administered systemically or topically, depending on such considerations as the condition to be treated, need for site-specific treatment, quantity of drug to be administered, and numerous other considerations. Thus, in the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pennsylvania. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses' medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 0.01 and 5 mg per kg of body weight per day would be expected to effect a therapeutic result in the treatment of many diseases for which these compounds are useful.

GENERAL EMBODIMENTS AND SYNTHETIC METHODOLOGY

Definitions

The term alkyl refers to and covers any and all groups which are known as normal alkyl, branched-chain alkyl, cycloalkyl and also cycloalkyl-alkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Unless specified otherwise, lower alkyl means the above-defined broad definition of alkyl groups having 1 to 6 carbons in case of normal lower alkyl, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo-lower alkenyl groups. Lower alkynyl is also defined similarly, having 2 to 6 carbons for normal lower alkynyl groups, and 4 to 6 carbons for branch chained lower alkynyl groups.

The term "ester" as used here refers to and covers any compound falling within the definition of that term as classically used in organic chemistry. It includes organic and inorganic esters. Where B of Formula 1 is —COOH, this term covers the products derived from treatment of this function with alcohols or thiols preferably with aliphatic alcohols having 1–6 carbons. Where the ester is derived from compounds where B is —CH$_2$OH, this term covers compounds derived from organic acids capable of forming esters including phosphorous based and sulfur based acids, or compounds of the formula —CH$_2$OCOR$_{11}$, where R$_{11}$ is any substituted or unsubstituted aliphatic, aromatic, heteroaromatic or aliphatic aromatic group, preferably with 1–6 carbons in the aliphatic portions.

Unless stated otherwise in this application, preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

The term amides has the meaning classically accorded that term in organic chemistry. In this instance it includes the unsubstituted amides and all aliphatic and aromatic mono- and di-substituted amides. Unless stated otherwise in this application, preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and disubstituted amides derived from the substituted and unsubstituted phenyl or lower alkylphenyl amines. Unsubstituted amides are also preferred.

Acetals and ketals include the radicals of the formula -CK where K is (—OR)$_2$. Here, R is lower alkyl. Also, K may be —OR$_7$O— where R$_7$ is lower alkyl of 2–5 carbon atoms, straight chain or branched.

A pharmaceutically acceptable salt may be prepared for any compound in this invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri- acid may also be used.

The compounds of the present invention are capable of existing as trans and cis (E and Z) isomers relative to olephinic double bonds, and in case of the preferred compounds relative to a cyclopropane ring as well. Unless specific orientation of substituents relative to a double bond or the ring is indicated in the name of the respective compound, and/or by specific showing in the structural formula of the orientation of the substituents relative to the double bond or ring, the invention covers trans as well as cis isomers relative to each center that gives rise to such isomerism.

Some of the compounds of the present invention may contain one or more chiral centers and therefore may exist in enantiomeric and diastereomeric forms. The scope of the present invention is intended to cover all isomers per se, as well as mixtures of cis and trans isomers, mixtures of diastereomers and racemic mixtures of enantiomers (optical isomers) as well. The compounds of the invention where the variable Y of Formula 1 represents a bivalent cyclopropyl radical can, generally speaking, be obtained by a series of reactions disclosed in Reaction Scheme 1. Referring now to this scheme, the starting compound in this synthetic route is a compound of Formula 2, which is a phenol, thiophenol or aniline derivative substituted in the 4 (para) position with a bromo group, in the 2 (ortho) position with a carboxylic acid, and may also be optionally substituted with one or more $R_3$ groups. The nature of the optional $R_3$ group is defined in connection with Formula 1. Compounds of Formula 2 are available commercially and/or can be prepared in accordance with the chemical literature, or by such modifications of known synthetic procedures which are readily apparent to those skilled in the art. The compound of Formula 2 is esterified, to provide an ester, which in the generalized but nevertheless examplary synthetic procedure of Reaction Scheme 1 is an ethyl ester of Formula 3. The phenol, thiophenol or amino function of the ester compound of Formula 3 is then alkylated with an ot-bromo-carboxylic acid ester of the general formula $BrCHR'_2CO_2Et$ to provide the intermediate compounds of Formula 4. In $BrCHR'_2CO_2Et$ the $R'_2$ group is defined as in connection with Formula 1. The intermediate compounds of Formula 4 are then ring closed by treatement with strong base (for example NaOEt) to form the bromo benzofuranone, indanone or dihydrobenzothiophene 3-one derivatives of Formula 5.

The oxo function of the bromo benzofuranone, indanone or dihydiobenzothiophene 3-one derivatives of Formula 5 is reacted with a Grignard reagent of the formula $R_2MgBr$ where the variable $R_2$ is defined as in connection with Formula 1. The resulting tertiary alcohol of Formula 6 is dehydrated by treatment with acid to provide the intermediate bromo-benzofuran, bromoindole or bromobenzothiophene compounds of Formula 7. The bromo function of the intermediate compounds of Formula 7 is converted to the dihydroxyboron functionality of the compounds of Formula 8, by reaction with trimethoxyboron in the presence of t-butyl lithium. The dihydroxyboron derivative of Formula 8 is reacted with a reagent of the formula $R_4IC=CH-CH_2OH$ where the variable $R_4$ is defined as in connection with Formula 1. Preferrably the variable $R_4$ represents hydrogen or an alkyl group, most preferably methyl. The reaction with the reagent $R_4IC=CH-CH_2OH$ is conducted in the presence of tetrakis Pd(0)triphenylphosphine catalyst in an aprotic solvent, to give the vinyl alcohol intermediate of Formula 9. The vinylic double bond of the intermediate of Formula 9 is reacted with diidomethane in the presence of diethyl zinc, and (4S,5S)-2-butyl-N, N,N,N-tetramethyl [1,3,2-]dioxaborolane-[4,5]dicarboxamide which can be prepared in accordance with the teaching of *J. Amer. Chem. Soc.* 1998, 120, 11943 (incorporated herein by reference). As is known, the cyclopropylation reaction with diiodomethane preserves the cis or trans stereochemistry of the double bond to which the "$CH_2$" moiety is added. Thus, depending on the cis or trans nature of the reagent $R_4IC=CH-CH_2OH$ either cis or trans stereochemistry relative to the cyclopropane ring can be obtained. Reaction Scheme 1 shows only one such compound (Formula 10) which is cis. The reagent levorotatory (4S,5S)-2-butyl-N,N,N,N-tetramethyl[1,3,2-]dioxaborolane-[4,5]dicarboxamide causes the reaction to provide a mixture of enantiomers wherein one of the two enantiomers predominates but is not the exclusive product. In order to obtain predominantly the other enantiomer the dextrorotatory form of the reagent would be used.

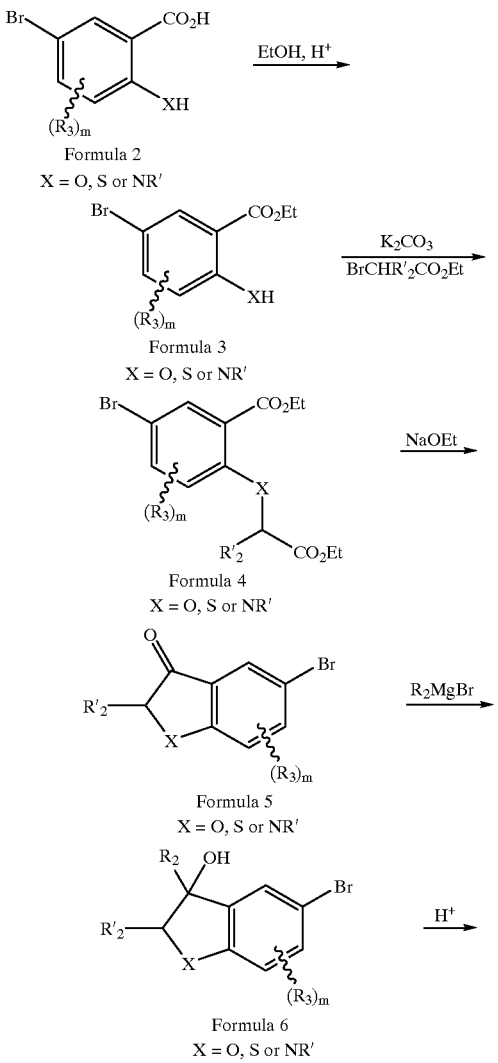

REACTION SCHEME 1

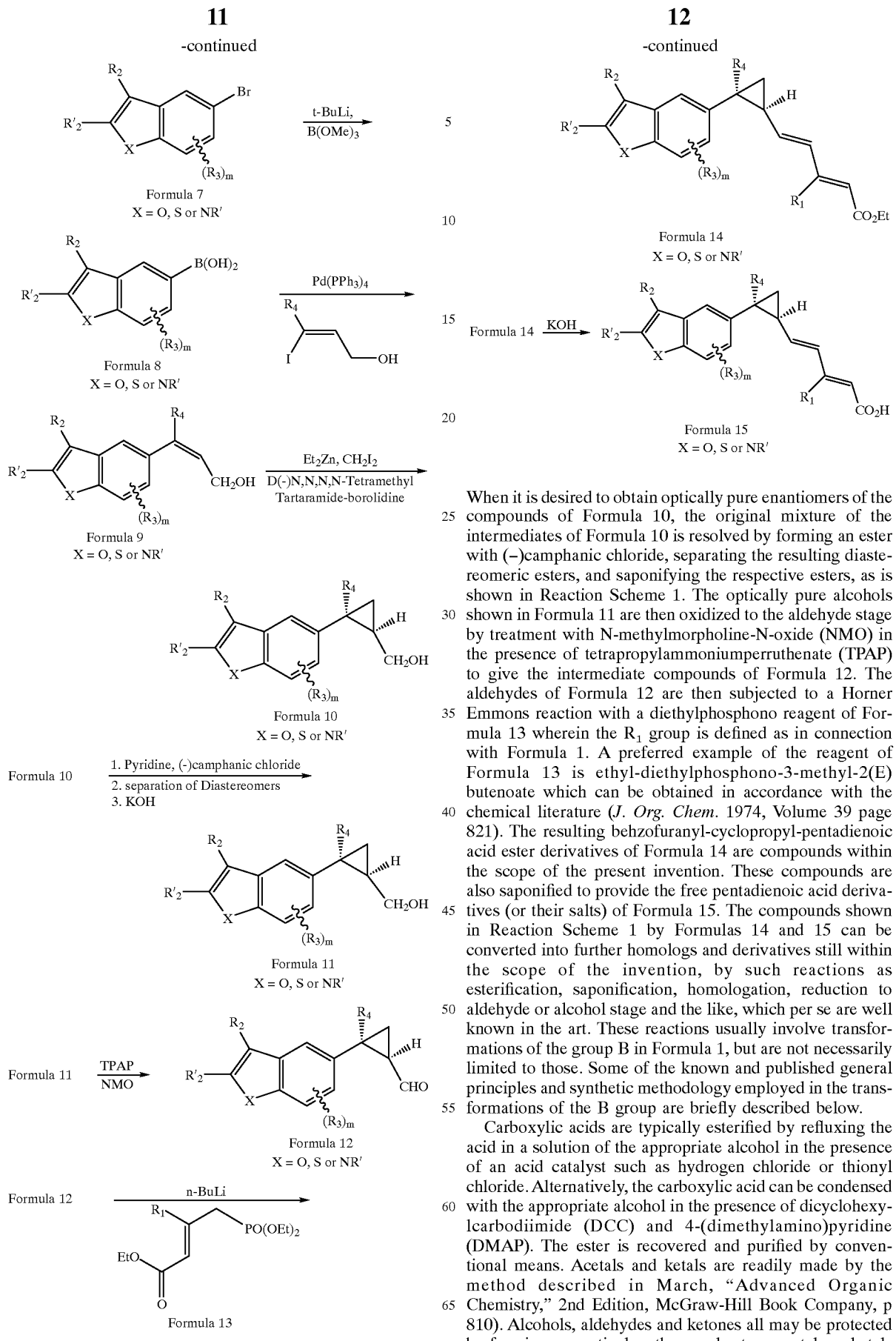

When it is desired to obtain optically pure enantiomers of the compounds of Formula 10, the original mixture of the intermediates of Formula 10 is resolved by forming an ester with (−)camphanic chloride, separating the resulting diastereomeric esters, and saponifying the respective esters, as is shown in Reaction Scheme 1. The optically pure alcohols shown in Formula 11 are then oxidized to the aldehyde stage by treatment with N-methylmorpholine-N-oxide (NMO) in the presence of tetrapropylammoniumperruthenate (TPAP) to give the intermediate compounds of Formula 12. The aldehydes of Formula 12 are then subjected to a Horner Emmons reaction with a diethylphosphono reagent of Formula 13 wherein the $R_1$ group is defined as in connection with Formula 1. A preferred example of the reagent of Formula 13 is ethyl-diethylphosphono-3-methyl-2(E) butenoate which can be obtained in accordance with the chemical literature (*J. Org. Chem.* 1974, Volume 39 page 821). The resulting behzofuranyl-cyclopropyl-pentadienoic acid ester derivatives of Formula 14 are compounds within the scope of the present invention. These compounds are also saponified to provide the free pentadienoic acid derivatives (or their salts) of Formula 15. The compounds shown in Reaction Scheme 1 by Formulas 14 and 15 can be converted into further homologs and derivatives still within the scope of the invention, by such reactions as esterification, saponification, homologation, reduction to aldehyde or alcohol stage and the like, which per se are well known in the art. These reactions usually involve transformations of the group B in Formula 1, but are not necessarily limited to those. Some of the known and published general principles and synthetic methodology employed in the transformations of the B group are briefly described below.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide (DCC) and 4-(dimethylamino)pyridine (DMAP). The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

The acids and salts derived from compounds of the invention are readily obtainable from the corresponding esters. Basic saponification with an alkali metal base will provide the acid. For example, an ester of the invention may be dissolved in a polar solvent such as an alkanol, preferably under an inert atmosphere at room temperature, with about a three molar excess of base, for example, lithium hydroxide or potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the ester is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, ibid, pg. 1124), which gives the corresponding alcohols. Alternatively, esters may be reduced with lithium aluminum hydride at reduced temperatures. Alkylating these alcohols with appropriate alkyl halides under Williamson reaction conditions (March, ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swern, D., *Tetrahedron*, 1978 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, ibid, p 810.

The compounds of the invention where the variable Y of Formula 1 represents a bivalent aryl or heteroaryl radical can, generally speaking, be obtained by a series of reactions disclosed in Reaction Scheme 2. In accordance with this scheme the dihydroxyboron derivative of Formula 8 (obtained as disclosed in Reaction Scheme 1) is reacted with an aryl or heteroaryl compound of the formula $Y(R_4)BrZ$ where the variable Y is defined as an aryl or heteroaryl group as further defined in connection with Formula 1, $R_4$ is defined as in connection with Formula 1 and Z represents a cyano (CN) function, or an esterified carboxylic acid, such as COOEt. Instead of the bromo function, another halogen or other moiety capable of acting as a leaving group in the coupling reaction catalyzed by tetrakis Pd(0) triphenylphosphine could be present in the reagent.

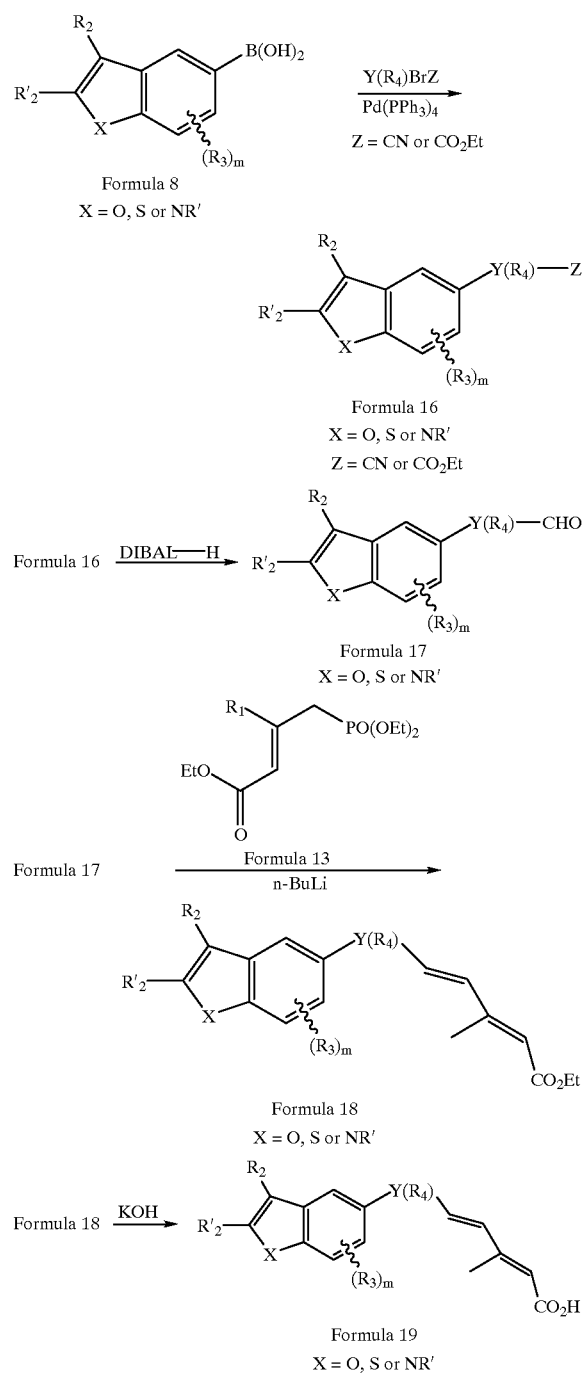

Reagents of the formula $Y(R_4)BrZ$ (or analogous reagents as noted above) are readily available in accordance with the chemical literature, or can be made by such modifications of known chemical reactions which are readily apparent to those skilled in the art. Some reagents of the formula Y(R₄)BrZ are available commercially. Preferably, the bromo atom (or other leaving group functionality) and the group designated by the variable Z are on adjacent carbons in the aromatic or heteroaromatic ring designated Y. Examples for such preferred reagents of formula Y(R₄)BrZ are ethyl-2-bromobenzoate, ethyl-2-bromopyridine-3-carboxylate, ethyl 2-bromothiophene-3-carboxylate and ethyl 2-bromofuran-3-carboxylate. Instead of the ethyl carboxylates, the corresponding cyanoderivatives can also serve as suitable reagents.

As is shown in Reaction Scheme 2 the product of the reaction between the dihydroxy boron derivative of Formula 8 and the reagent of the formula Y(R₄)BrZ is a benzofuranyl, benzothienyl or indolyl aryl (or heteroaryl) carboxylic acid ester or cyano compound of Formula 16. The compound of Formula 16 is reduced with di-isobutyl aluminumhydride to the aldehydes of Formula 17. The aldehyde of Formula 17 is then reacted with the reagent of Formula 13 in a Horner Emmons reaction. This latter Homer Emmons reaction, and the subsequent steps in this synthetic scheme are analogous to the steps described in connection with Reaction Scheme 1 and do not need to be described here again.

SPECIFIC EMBODIMENTS

With reference to the symbol Y in Formula 1 the preferred compounds of the invention are those where Y is cyclopropyl. Compounds are also preferred where Y a bivalent phenyl, naphthyl, pyridyl, thienyl or furyl radical, substituted on adjacent carbons respectively with the pentadienoic acid and the bezofuranyl, indolyl or benzothienyl groups. In the presently preferred compounds of the invention the R₄ substituent on the cyclopropyl group is methyl, and there is only one methyl substituent on the cyclopropyl ring.

The compounds preferably are benzofuran derivatives, so that the variable X is preferably oxygen (O).

The B group of the preferred compounds is COOH or COOR₈, where R₈ is defined as above. Even more preferably R₈ is alkyl of 1 to 6 carbons, or the compound is a carboxylic acid, or a pharmaceutically acceptable salt thereof.

R₁ is preferably H or an alkyl group of 1 to 6 carbons. Even more preferably R₁ is H or methyl.

The R₂ and R'₂ groups are preferably alkyl of 1 to 6 carbons. Ethyl, pentyl, iso-propyl and tertiary-butyl groups are also preferred for one or both of the R₂ and R'₂ groups.

The R₃ group is preferably hydrogen or alkyl of 1 to 6 carbons, even more preferably hydrogen or methyl.

The presently most preferred compounds of the invention are disclosed in Table 2 with reference to Formula 20.

Formula 20

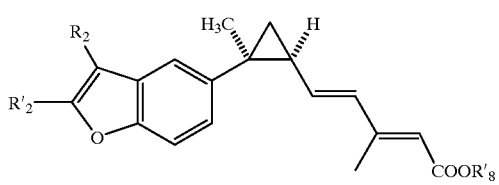

TABLE 2

| Compound # | R₂ | R'₂ | R'₈ |
|---|---|---|---|
| 10 | t-butyl | ethyl | ethyl |
| 12 | t-butyl | ethyl | H |
| 19 | ethyl | ethyl | ethyl |
| 20 | ethyl | ethyl | H |
| 27 | i-propyl | ethyl | ethyl |
| 28 | i-propyl | ethyl | H |
| 37 | t-butyl | n-pentyl | ethyl |
| 38 | t-butyl | n-pentyl | H |

A detailed description of the steps of the processes illustrated in Reaction Scheme 1 as utilized for the preparation of the presently preferred examples of the invention is provided in the experimental section of this application for patent.

SPECIFIC EXAMPLES

Ethyl-5-bromosalicylate (Compound 1)

To 5-bromosalicylic acid (25 g, 115 mmol) in ethyl alcohol (300 mL) was added sulfuric acid (98%, 2 mL). The mixture was refluxed in a Dean-Stark apparatus for 2 days. The reaction mixture was cooled to room temperature. Most of the ethyl alcohol was removed by distillation. The residue was diluted with ethyl acetate, washed with water, aq. Na₂CO₃ and brine. The organic layer was dried (Na₂SO₄) and the solvent was removed to afford the title compound as a white solid.

$^1$H NMR (300 MHz, CDCl₃): δ 1.41 (t, J=6.9 Hz, 3H), 4.38 (q, J=7.0 Hz, 2H), 6.83 (d, J=8.2 Hz, 1H), 7.48 (d, J=8.2 Hz, 1H), 7.93 (s, 1H), 10.8 (s, 1H).

Ethyl-2-oxo-[ethyl-5-bromo-salicylate-2-yl]-butyrate (Compound 2)

To a solution of ethyl-5-bromo-salicylate (Compound 1, 20 g, 82 mmol) in acetone (300 mL), ethyl-2-bromo-butyrate (47.7 g, 246 mmol) and K₂CO₃ (34.5 g, 250 mmol) were added and the mixture stirred for 24 h. Solid material was removed by filtration and the solvent was removed by distillation to yield the title compound as a yellow oil.

$^1$H NMR (CDCl₃): δ 1.12 (t, J=7.3 Hz, 3H), 1.28 (t, J=7.5 Hz, 3H), 1.40 (t, J=7.5 Hz, 3H), 2.00–2.12 (m, 2H), 4.20 (q, J=7.5 Hz, 2H), 4.35 (q, J=7.5 Hz, 2H), 4.55 (t, J=5.5 Hz, 1H), 6.68 (d, J=8.5 Hz, 1H), 7.48 (dd, J=2.9, 8.5 Hz, 1H), 7.90 (d, J=2.0 Hz, 1H).

5-Bromo-2-ethyl-benzofuran(2H)-3-one (Compound 3)

To a cold (0° C.) solution of ethyl-2-oxo-[ethyl-5-bromo-salicylate-2-yl]-butyrate (Compound 2, 29 g, 81 mmol) in benzene (300 mL) was added sodium ethoxide (4.4 g, 64.5 mmol) in small portions (5 mins). The cooling bath was removed and the reaction was stirred at ambient temperature for 2 h. The reaction mixture was washed with water (25 mL) and brine (50 mL). The organic layer was dried and the solvent was removed by evaporation. The crude product was purified by column chromatography to afford the title compound as a white solid.

$^1$H NMR (CDCl₃): δ 1.03 (t, J=7.3 Hz, 3H), 1.75–1.90 (m, 1H), 1.98–2.15 (m, 1H), 4.57 (dd, J=4.5, 9.5 Hz, 1H), 7.04 (d, J=8.8 Hz, 1H), 7.68 (dd, J=2.1, 8.8 Hz, 1H), 7.77 (d, J=2.1 Hz, 1H).

5-Bromo-3-t-butyl-2-ethyl-benzofuran (Compound 4)

To a cold (−78° C.) suspension of CeCl₃ (2.25 g, 9.1 mmol) in THF (25 mL) was added t-BuMgCl in THF (1M solution, 9.2 mL), and the resulting mixture stirred for 30 min. Then 5-bromo-2-ethyl-benzofuran(2H)-3-one (3) (960 mg, 4 mmol) in THF (10 mL) was added and the mixture stirred at ambient temperature for 30 min. The reaction was quenched by adding MeOH at −78° C., diluted with ethyl acetate (100 mL), washed with aq. $NH_4Cl$, water and brine (20 mL each). The organic layer was dried and the solvent was removed by distillation. The resulting residue was a mixture of the tertiary alcohol and of the reacted ketone, and the mixture was used in the next step without further purification.

A mixture of the crude tertiary alcohol (obtained above), dichloromethane (30 mL) and pTSA (20 mg) was stirred for 12 h at ambient temperature. The mixture was washed with aq. $NaHCO_3$, water and brine (10 mL each). The organic layer was dried and the solvent was removed by distillation. The residual crude product was purified by flash chromatography (3% ethyl acetate in hexane) to afford the title compound as a colorless oil.

$^1$H NMR ($CDCl_3$): δ 1.31 (t, J=7.3 Hz, 3H), 1.48 (s, 9H), 2.90 (q, J=7.3 Hz, 2H), 7.22 (d, J=8.5 Hz, 1H), 7.28 (dd, J=2.0, 8.5 Hz, 1H), 7.80 (d, J=Hz, 1H).

3-(3-t-butyl-2-ethyl-benzofur-5-yl)-but-2(Z)-en-1-ol (Compound 6)

To a cold (−78° C.) solution of 5-bromo-3-t-butyl-2-ethyl-benzofuran (4) (200 mg, 0.71 mmol) in THF (6 mL) was added t-BuLi in pentane (1.7M solution, 0.9 mL, 1.56 mmol). The mixture was gradually warmed to approximately 10° C. over 50 min, then cooled again to −78° C. and $B(OMe)_3$ (156 mg, 1.56 mmol) was added via syringe (neat). Cooling was removed and the reaction was stirred at ambient temperature for 15 min. The reaction was quenched by adding aq. $NH_4Cl$, and the mixture was stirred for 15 min. The mixture was diluted with ethyl acetate (60 mL) washed with water and brine (10 mL each). The organic layer was dried and the solvent was removed by distillation. The resulting residue was the dihydroxy boron derivative (Compound 5) in crude form. It was used in the next step without further purification.

Argon was bubbled for two minutes into a mixture of Compound 5 (from the above reaction), toluene (8 mL), MeOH (2 mL), $K_2CO_3$ (200 mg), water (1 mL) and of 3-iodo-but-2-(Z)-en-1-ol (200 mg, 1 mmol). To this mixture $Pd(PPh_3)_4$ (5 mg) was added and the mixture was heated to 90° C. for 16 h. The reaction mixture was then diluted with ethyl acetate (50 mL), washed with water and brine (10 mL each). The organic layer was dried and the solvent was removed by distillation. The title Compound 6 was obtained as a colorless oil by column chromatography (10% ethylacetate in hexane).

$^1$H NMR ($CDCl_3$): δ 1.30 (t, J=7.8 Hz, 3H), 1.49 (s, 9H), 2.15 (s, 3H), 2.93 (q, J=7.8 Hz, 2H), 4.13 (d, J=6.6 Hz, 2H), 5.74 (t, J=6.6 Hz, 1H), 7.02 (dd, J=1.7, 8.5 Hz, 1H), 7.33 (d, J=8.5 Hz, 1H), 7.51 (d, J=1.7 Hz, 1H).

2(R),3(S)-Methano-3(3-t-butyl-2-ethyl-benzofur-5-yl)-butan-1-ol (Compound 8)

To a cold (−60° C.) solution of $Et_2Zn-CH_2Cl_2$ (1.34 M solution, 5.1 mL, 6.7 mmol) was added dimethoxyethane (DME) via syringe. To this solution diiodomethane (3.6 g, 13.3 mmol) was added dropwise over 20 min. This diethyl zinc reagent was canulated into another flask containing 3-(3-t-butyl-2-ethyl-benzofur-5-yl)-but-2(Z)-en-1-ol (Compound 6, 40 mg, 0.15 mmol), (4S,5S)-2-butyl-N,N,N, N-tetramethyl[1,3,2-]dioxaborolane-[4,5]dicarboxamide (Compound 7, prepared according to *J. Amer. Chem. Soc.* 1998, 120, 11943; 100 mg, 0.37 mmol), mol. sieves (500 mg), dichloromethane (5 mL) at −78° C. The reaction mixture was stirred for 18 h while the temperature was kept between −25° C. and −15° C. The reaction was quenched by adding aq. $NH_4Cl$, diluted- with ethylacetate (100 mL). The organic layer was washed with water and brine (20 mL each), dried and the solvent was removed by distillation. Flash chromatography (20% ethylacetate in hexane) gave the title compound as a colorless oil.

$^1$H NMR ($CDCl_3$): δ 0.80–0.95 (m, 2H), 1.31 (t, J=7.4 Hz, 3H), 1.35–1.40 (m, 1H), 1.45 (s, 3H), 1.50 (s, 9H), 2.90 (q, J=7.4 Hz, 2H), 3.20–3.35 (m, 2H), 7.19 (dd, J=1.8, 8.4 Hz, 1H), 7.30 (d, J=8.4 Hz, 1H), 7.67 (d, J=1.8 Hz, 1H).

2(R),3(S)-Methano-3(3-t-butyl-2-ethyl-benzofur-5-yl)-butanal (Compound 9)

To a mixture of 2(R),3(S)-methano-3-t-butyl-2-ethyl-benzofur-5-yl)-butan-1-ol (Compound 8, 28 mg, 0.11 mmol), dichloromethane (5 mL), mol.sieves (500 mg), and N-methylmorpholine-N-oxide (NMO) (45 mg, 0.38 mmol), was added tetrapropylammoniumperruthenate (TPAP, 2 mg) and the mixture was stirred at ambient temperature. The reaction was followed by TLC every 10 minutes. The reaction was complete in 20 min. The mixture was loaded on a silicagel column without any purification and the column was eluted with 10% ethylacetate in hexane to afford the title compound as colorless oil.

$^1$H NMR ($CDCl_3$): δ 1.29 (t, J=7.6 Hz, 3H), 1.49 (s, 9H), 1.51 (s, 3H), 1.45–1.55 (m, 1H), 1.90–2.02 (m, 2H), 2.91 (q, J=7.6 Hz, 2H), 7.16 (dd, J=1.7, 8.4 Hz, 1H), 7.30 (d, J=8.4 Hz, 1H), 7.65 (d, J=1.7 Hz, 1H), 8.45 (d, J=7.1 Hz, 1H).

Ethyl-3-methyl-6(S),7(S)-methano-7-(3-t-butyl-2-ethyl-benzofur-5-yl)-octa-2(E),4(E)-dienoate (Compound 10)

To a cold (−78° C.) solution of ethyl-diethylphosphono-3-methyl-2(E)butenoate (Compound 11, 750 mg, 2.8 mmol), and 1,3-dimethyl-3,4,5,6-tetrahydro-2(1H)-pyrimidinone (DMPU, 1 mL) in THF (10 mL) was added n-BuLi (1.6 M solution, 1.9 mL, 3 mmol). The mixture was stirred for 5 minutes at −78° C. To this mixture 2(R),3(S)-methano-3(3-t-butyl-2-ethyl-benzofur-5-yl)-butanal (Compound 9, 27 mg, 0.095 mmol) in THF (2 mL) was added and the reaction mixture was warmed gradually to −10° C. The reaction was quenched by adding water (10 mL) diluted with ethylacetate (70 mL). The organic layer was washed with brine (10 mL), dried and the solvent was removed by evaporation. Flash chromatography followed by HPLC purification (Partisil-10 semiprep column; 5 mL/min flow rate) gave the title compound as a colorless oil.

$^1$H NMR ($CDCl_3$): δ 1.15 (t, J=4.8 Hz, 1H), 1.28 (t, J=7.1 Hz, 3H), 1.30 (t, J=7.4 Hz, 3H), 1.25–1.34 (m, 1H), 1.46 (s, 3H), 1.47 (s, 9H), 1.75–1.83 (m, 1H), 1.96 (s, 3H), 2.92 (q, J=7.4 Hz, 2H), 4.14 (q, J=7.1 Hz, 2H), 5.26 (dd, J=10.0, 15.5 Hz, 1H), 5.65 (s, 1H), 6.25 (d, J=15.5 Hz, 1H), 7.10 (dd, J=1.6, 8.9 Hz, 1H), 7.28 (d, J=8.9 Hz, 1H), 7.56 (d, J=1.6 Hz, 1H).

3-Methyl-6(S),7(S)-methano-7-(3-t-butyl-2-ethyl-benzofur-5-yl)-octa-2(E),4(E)-dienoic acid (Compound 12)

A solution of ethyl-3-methyl-6(S),7(S)-methano-7-(3-t-butyl-2-ethyl-benzofur-5-yl)-octa-2(E),4(E)-dienoate (Compound 10, 31 mg, 0.08 mmol), THF (3 mL), MeOH (2 mL), KOH-water (1M solution, 0.4 mL, 0.4 mmol) were heated to 50° C. for 15h. The reaction was diluted with ethylacetate (30 mL), acidified with 10% HCl, washed with water and brine (5 mL each). The organic layer was dried and the solvent was removed by evaporation. Flash chromatography with 25% ethyl acetate in hexane gave the title compound as a white solid.

$^1$H NMR (CDCl$_3$): δ 1.17 (t, J=4.9 Hz, 1H), 1.27 (t, J=4.0 Hz, 1H), 1.30 (t, J=7.4 Hz, 3H), 1.46 (s, 3H), 1.47 (s, 9H), 1.76–1.85 (m, 1H), 1.96 (s, 3H), 2.92 (q, J=7.4 Hz, 2H), 5.31 (dd, J=10.0, 15.6 Hz, 1H), 5.66 (s, 1H), 6.28 (d, J=15.6 Hz, 1H), 7.10 (dd, J=1.7, 8.5 Hz, 1H), 7.29 (d, J=8.5 Hz, 1H), 7.55 (d, J=1.7 Hz, 1H).

5-Bromo-2,3-diethyl-benzofuran (Compound 13)

To CeCl$_3$ (3 g, 12.4 mmol) was added THF (40 mL). The suspension was cooled to 0° C. and EtMgBr (3M, 4.1 mL, 12.4 mmol) was added dropwise. The mixture was stirred for one hour at 0° C. then 5-bromo-2-ethyl-benzofuran(2H)-3-one (Compound 3, 2 g, 8.2 mmol) in THF (15 mL) was added dropwise. The cooling was discontinued and the reaction mixture was stirred at ambient temperature for 20 hours. The mixture was poured into ice with aqueous 2% HCl solution and diluted with diethyl ether. The organic layer was washed with water and brine, dried and the solvent was removed by evaporation. The resulting residue was the crude tertiary alcohol which was in the next reaction without further purification.

The crude tertiary alcohol from the above reaction was converted to the title compound by using the procedure used for the preparation of 5-bromo-3-t-butyl-2-ethyl-benzofuran (Compound 4).

$^1$H NMR (300 MHz, CDCl$_3$): δ 1.22 (m, 3H), 1.29 (m, 3H), 2.59 (q, J=7.6 Hz, 2H), 2.74 (q, J=7.5 Hz, 2H), 7.26 (m, 2H), 7.58 (s, 1H).

3-(2,3-diethyl-benzofur-5-yl)-but-2(Z)-en-1-ol (Compound 15)

By following the procedure used for the preparation of 3-(3-t-butyl-2-ethyl-benzofur-5-yl)-but-2(Z)-en-1-ol (Compound 6), Compound 13 was converted into the title Compound 15.

$^1$H NMR (300 MHz, CDCl$_3$) δ 1.24 (m, 3H), 1.30 (m, 3H), 2.13 (s, 3H), 2.63 (q, J=7.6 Hz, 2H), 2.75 (q, J=7.5 Hz, 2H), 4.12 (m, 2H), 5.74 (m, 1H), 7.03 (d, J=8.2 Hz, 1H), 7.26 (s, 1H), 7.34 (d, J=8.2 Hz, 1H).

2(R),3(S)-Methano-3(2,3-diethyl-benzofur-5-yl)-butan-1-ol (Compound 16)

By using the procedure used for the preparation of 2(R),3(S)-methano-3(3-t-butyl-2-ethyl-benzofur-5-yl)-butan-1-ol (Compound 8), Compound 15 was converted into the title compound 16.

A mixture of Compound 16 (97 mg), CH$_2$Cl2 (4ml), 1(s)-camphanic chloride (257 mg, 3.2eq), triethylamine (3 ml), and dimethylaminopyridine (DMAP) (20 mg) was heated to 55° C. for 16 h. The reaction mixture was diluted with diethyl ether, washed with water, NaHCO$_3$ (sat.) and brine. The organic layer was dried and the solvent was removed by evaporation. Purification by silica gel column chromatography gave 294 mg white solid, which was further purified by HPLC (Normal phase, 6% EtOAc/Hexane) to give 133 mg of the camphenoate ester (Compound 17) as a clear oil.

$^1$H NMR (300 MHz, CDCl$_3$): δ 0.92–1.04 (m, 3H), 0.97 (s, 3H), 1.05 (s, 3H), 1.14 (s, 3H), 1.23–1.32 (m, 6H), 1.46 (s, 3H), 1.63–1.74 (m, 1H), 1.88–2.04 (m, 2H), 2.34–2.44 (m, 1H), 2.65 (q, J=7.5 Hz, 2H), 2.75 (q, J=7.5 Hz, 2H), 3.83 (dd, J=7.5, 11.5 Hz, 1H), 3.91 (dd, J=7.5, 11.5 Hz, 1H), 7.17 (d, J=8.3 Hz, 1H), 7.30 (d, J=8.3 Hz, 1H), 7.39 (s, 1H)

2(R),3(S)-Methano-3(2,3-diethyl-benzofur-5-yl)-butan-1-ol (Compound 16)

To a solution of camphenoate ester (Compound 17, 133 mg) in THF (6 ml) and MeOH (4 ml) was added KOH (1.1 ml, 1M solution in H$_2$O). The mixture was heated to 75° for two hours, cooled to ambient temperature. The THF and MeOH solvents were removed by evaporation under reduced pressure. The residue was diluted with water and extracted with diethyl ether. The combined ether layers were washed with water and brine and dried. The solvent was removed by evaporation to give 52 mg, 67% the title compound as a clear oil.

$^1$H NMR (300 MHz, CDCl$_3$): δ 0.80–0.84 (m, 1H), 0.90–0.93 (m, 1H), 1.21–1.32 (m, 7H), 1.43 (s, 3H), 2.63 (q, J=7.5 Hz, 2H), 2.73 (q, J=7.5 Hz, 2H), 3.23 (m, 2H), 7.17 (d, J=8.2 Hz, 1H), 7.30 (d, J=8.2 Hz, 1H), 7.40 (s, 1H).

2(R),3(S)-Methano-3(2,3-diethyl-benzofur-5-yl)-butanal (Compound 18)

By following the procedure used for the preparation of 2(R),3(S)-methano-3(3-t-butyl-2-ethyl-benzofur-5-yl)-butanal (Compound 9), 2(R),3(S)-methano-3(2,3-diethyl-benzofur-5-yl)-butan-1-ol (Compound 16) was converted into the title compound.

$^1$H NMR (300 MHz, CDCl$_3$): δ 1.22–1.32 (m, 6H), 1.46–1.52 (m, 4H), 1.94–1.99 (m, 2H), 2.64 (q, J=7.5 Hz, 2H), 2.75 (q, J=7.5 Hz, 2H), 7.18 (d, J=8.3 Hz, 1H), 7.33 (d, J=8.3 Hz, 1H), 7.42 (s, 1H), 8.44 (d, J=6.9 Hz, 1H).

Ethyl-3-methyl-6(S),7(S)-methano-7-(2,3-diethyl-benzofur-5-yl)-octa-2(E),4(E)-dienoate (Compound 19)

By following the procedure used for the preparation of ethyl-3-methyl-6(S),7(S)-methano-7-(3-t-butyl-2-ethyl-benzofur-5-yl)-octa-2(E),4(E)-dienoate (Compound 10), 2(R),3(S)-Methano-3(2,3-diethyl-benzofur-5-yl)-butanal (Compound 18) was converted into the title compound.

$^1$H NMR (300 MHz, CDCl$_3$): δ 1.17–1.32 (m, 11H), 1.45 (s, 3H), 1.79 (m, 1H), 1.96 (s, 3H), 2.62 (q, J=7.5 Hz, 2H), 2.74 (q, J=7.5 Hz, 2H), 4.14 (q, J=4.1 Hz, 2H), 5.24 (dd, J=10.1, 15.5 Hz, 1H), 5.64 (s, 1H), 6.23 (d, J=15.5 Hz, 1H), 7.10 (d, J=8.3 Hz, 1H), 7.30 (d, J=8.3 Hz, 1H), 7.34 (s, 1H).

3-Methyl-6(S),7(S)-methano-7-(2,3-di-ethyl-benzofur-5-yl)-octa-2(E),4(E)-dienoic acid (Compound 20)

By following the procedure used for the preparation of 3-methyl-6(S),7(S)-methano-7-(3-t-butyl-2-ethyl-benzofur-5-yl)-octa-2(E),4(E)-dienoic acid (Compound 12), ethyl-3-methyl-6(S),7(S)-methano-7-(2,3-diethyl-benzofur-5-yl)-octa-2(E),4(E)-dienoate (Compound 19) was converted into the title compound.

$^1$H NMR (300 MHz, CDCl$_3$): δ 1.19–1.29 (m, 8H), 1.45 (s, 3H), 1.77–1.83 (m, 1H), 1.95 (s, 3H), 2.62 (q, J=7.5 Hz, 2H), 2.75 (q, J=7.5 Hz, 2H), 5.29 (dd, J=10.0, 15.4 Hz, 1H), 5.65 (s, 1H), 6.26 (d, J=15.4 Hz, 1H), 7.10 (d, J=8.3 Hz, 1H), 7.30 (d, J=8.3 Hz, 1H), 7.34 (s, 1H).

5-Bromo-2-ethyl-3-iso-propyl-benzofuran (Compound 21)

By following the procedure used for the preparation of 5-bromo-2,3-diethyl-benzofuran (Compound 13), 5-bromo- 2-ethyl-benzofuran(2H)-3-one (Compound 3) was converted into the title compound.

$^1$H NMR (CDCl$_3$): δ 1.29 (m, 3H), 1.38 (d, J=7.1 Hz, 6H), 2.77 (q, J=7.5 Hz, 2H), 3.06 (m, 1H), 7.28 (m, 2H), 7.72 (s, 1H).

3-(2-ethyl-3-iso-propyl-benzofur-5-yl)-but-2(Z)-en-1-ol (Compound 23)

By following the procedure used for the preparation of 3-(3-t-butyl-2-ethyl-benzofur-5-yl)-but-2(Z)-en-1-ol (Compound 6), Compound 21 was converted into the title compound.

$^1$H NMR (300 MHz, CDCl$_3$): δ 1.28 (m, 3H), 1.38 (d, J=7.1 Hz, 6H), 2.13 (s, 3H), 2.75 (q, J=7.5 Hz, 2H), 3.07 (m, 1H), 4.12 (m, 2H), 5.75 (m, 1H), 7.00 (d, J=8.2 Hz, 1H), 7.33 (d, J=8.2 Hz, 1H), 7.38 (s, 1H).

2(R),3(S)-Methano-3(2-ethyl-3-iso-propyl-benzofur-5-yl)-butan-1-ol (Compound 24)

By using the procedure used for the preparation of 2(R),3(S)-methano-3(3-t-butyl-2-ethyl-benzofur-5-yl)-butan-1-ol (Compound 8), Compound 23 was converted into the title compound.

By following the procedure used for the preparation of camphenoate ester (Compound 17), 2(R),3(S)-methano-3(2-ethyl-3-iso-propyl-benzofur-5-yl)-butan-1-ol (Compound 24), was converted into the camphenoate ester. Compound 25, and the major diastereomer was separated by HPLC from the contaminating minor diastereomer.

$^1$H NMR (300 MHz, CDCl$_3$): δ 0.92–1.01 (m, 3H), 0.97 (s, 3H), 1.04 (s, 3H), 1.12 (s, 3H), 1.27 (m, 3H), 1.40 (d, J=7.1 Hz, 6H), 1.43 (s, 3H), 1.64–1.72 (m, 1H), 1.88–2.2 (m, 2H), 2.34–2.40 (m, 1H), 2.75 (q, J=7.5 Hz, 2H), 3.09 (m, 1H), 3.78 (dd, J=7.6, 11.4 Hz, 1H), 3.96 (dd, J=7.6, 11.4 Hz, 1H), 7.16 (d, J=8.2 Hz, 1H), 7.30 (d, J=8.2 Hz, 1H), 7.48 (s, 1H).

2(R),3(S)-Methano-3(2-ethyl-3-iso-propyl-benzofur-5-yl)-butan-1-ol (Compound 24)

By following the procedure used for the preparation of 2(R),3(S)-Methano-3(2,3-diethyl-benzofur-5-yl)-butan-1-ol (Compound 16), the camphenoate ester Compound 25 was converted into the title compound.

$^1$H NMR (300 MHz, CDCl$_3$): δ 0.82–0.94 (m, 3H), 1.28 (m, 3H), 1.40 (d, J=7.1 Hz, 6H), 1.45 (s, 3H), 2.75 (q, J=7.5 Hz, 2H), 3.08 (m, 1H), 3.27 (m, 2H), 7.18 (d, J=8.2 Hz, 1H), 7.32 (d, J=8.2 Hz, 1H), 7.52 (s, 1H).

2(R),3(S)-Methano-3(2,3-diethyl-benzofur-5-yl)-butanal (Compound 26)

By following the procedure used for the preparation of 2(R),3(S)-methano-3(3-t-butyl-2-ethyl-benzofur-5-yl)-butanal (Compound 9), 2(R),3(S)-methano-3(2-ethyl-3-iso-propyl-benzofur-5-yl)-butan-1-ol (Compound 24) was converted into the title compound.

$^1$H NMR (300 MHz, CDCl$_3$) δ 1.28 (m, 3H), 1.39 (d, J=7.1 Hz, 6H), 1.46–1.50 (m, 1H), 1.51 (s, 3H), 1.92–2.00 (m, 2H), 2.77 (q, J=7.5 Hz, 2H), 3.08 (m, 1H), 7.17 (d, J=8.2 Hz, 1H), 7.23 (d, J=8.2 Hz, 1H), 7.53 (s, 1H), 8.45 (d, J=7.0 Hz, 1H).

Ethyl-3-methyl-6(S),7(S)-methano-7-(2-ethyl-3-iso-propyl-benzofur-5-yl)-octa-2(E),4(E)-dienoate (Compound 27)

By following the procedure used for the preparation of ethyl-3-methyl-6(S),7(S)-methano-7-(3-t-butyl-2-ethyl-benzofur-5-yl)-octa-2(E),4(E)-dienoate (Compound 10), 2(R),3(S)-methano-3-(2-ethyl-3-iso-propyl-benzofur-5-yl)-butanal (Compound 26) was converted into the title compound.

$^1$H NMR (300 MHz, CDCl$_3$): δ 1.14 (m, 1H), 1.22–1.29 (m, 7H), 1.35 (m, 6H), 1.44 (s, 3H), 1.73–1.78 (m, 1H), 1.95 (s, 3H), 1.74 (q, J=7.5 Hz, 2H), 3.05 (m, 1H), 4.13 (q, J=7.1 Hz, 2H), 5.24 (dd, J=10.1, 15.5 Hz, 1H), 5.63 (s, 1H), 6.23 (d, J=15.5 Hz, 1H), 7.08 (d, J=8.2 Hz, 1H), 7.29 (d, J=8.2 Hz, 1H), 7.43 (s, 1H).

3-Methyl-6(S),7(S)-methano-7-(2-ethyl-3-iso-propyl-benzofur-5-yl)-octa-2(E),4(E)-dienoic acid (Compound 28)

By following the procedure used for the preparation of 3-methyl-6(S),7(S)-methano-7-(3-t-butyl-2-ethyl-benzofur-5-yl)-octa-2(E),4(E)-dienoic acid (Compound 12), ethyl-3-methyl-6(S),7(S)-methano-7-(2-ethyl-3-iso-propyl-benzofur-5-yl)-octa-2(E),4(E)-dienoate (Compound 27) was converted into the title compound.

$^1$H NMR (300 MHz, CDCl$_3$): δ 1.17 (m, 1H), 1.25–1.30 (m, 4H), 1.36 (m, 6H), 1.45 (s, 3H), 1.75–1.81 (m, 1H), 1.95 (s, 3H), 2.74 (q, J=7.5 Hz, 2H), 3.05 (m, 1H), 5.30 (dd, J=10.1, 15.5 Hz, 1H), 5.65 (s, 1H), 6.27 (d, J=15.5 Hz, 1H), 7.09 (d, J=8.2 Hz, 1H), 7.30 (d, J=8.2 Hz, 1H), 7.43 (s, 1H).

Ethyl-2-oxa-[ethyl-5-bromo-salicylate-2-yl]-heptanoate (Compound 29)

By following the procedure used for the preparation of ethyl-2-oxa-[ethyl-5-bromo-salicylate-2-yl]-butyrate (Compound 2), ethyl-5-bromosalicylate (Compound 1) was converted into the title compound.

$^1$H NMR (300 MHz, CDCl$_3$): δ 0.88 (m, 3H), 1.22 (m, 3H), 1.84 (m, 7H), 1.53 (m, 2H), 1.99 (m, 2H), 4.19 (q, J=7.1 Hz, 2H), 4.35 (q, J=7.1 hz, 2H), 4.60 (t, J=6.6 Hz, 1H), 6.6 (d, J=8.8 Hz, 1H), 7.46 (d, J=8.8 Hz, 1H), 7.89 (s, 1H).

5-Bromo-2-n-pentyl-benzofuran(2H)-3-one (Compound 30)

By following the procedure used for the preparation of 5-bromo-2-ethyl-benzofuran(2H)-3-one (Compound 3), ethyl-2-oxa-[ethyl-5-bromo-salicylate-2-yl]-heptanoate (Compound 29) was converted into the title compound.

$^1$H NMR (300 MHz, CDCl$_3$): δ 0.88 (m, 3H), 1.31 (m, 4H), 1.48 (m, 2H), 1.73 (m, 1H), 1.97 (m, 1H), 4.61 (m, 1H), 7.03 (d, J=8.8 Hz, 1H), 7.67 (d, J=8.8 Hz, 1H), 7.75 (s, 1H).

5-Bromo-2-n-pentyl-3-t-butyl-benzofuran (Compound 31)

By following the procedure used for the preparation of 5-bromo-2,3-diethyl-benzofuran (Compound 13), 5-bromo-2-n-pentyl-benzofuran(2H)-3-one (Compound 30) was converted into the title compound.

$^1$H NMR (300 MHz, CDCl$_3$): δ 0.92 (m, 3H), 1.36 (m, 4H), 1.48 (s, 9H), 1.72 (m, 2H), 2.88 (m, 2H), 7.26 (m, 2H), 7.83 (s, 1H).

3-(3-t-Butyl-2-pentyl-benzofur-5-yl)-but-2(Z)-en-1-ol (Compound 33)

To a solution of 5-bromo-2-n-pentyl-3-t-butyl-benzofuran (Compound 31, 256 mg, 0.79 mmol) in 5 mL DMF was added bis(pinacolato)diboron (232 mg, 0.91 mmol), KOAc (232 mg, 2.4 mmol) and [1,1'-bis(diphenylphosphino)-ferrocene]-dichloro palladium(II) complex with dichloromethane 1:1 (PdCl$_2$.dppf, 40 mg). The mixture was heated to 80° C. for 15 hours. Then the reaction mixture was cooled to room temperature and 3-iodo-but-2(Z)en-1-ol (312 mg, 1.58 mmol) in 3 mL DMF was cannulated to the mixture. Na$_2$CO$_3$(0.33 g) in water (1.8 ml) was added to the mixture. The mixture was heated at 80° C. for 8 hours. The mixture was cooled to ambient temperature and diluted with diethyl ether. The organic layer was washed with water and brine. The organic layer was dried and the solvent was removed by evaporation. The residual crude product was purified by silica gel column chromatography to afford the title compound.

$^1$H NMR (CDCl$_3$): δ 0.94 (m, 3H), 1.40 (m, 4H), 1.51 (s, 9H), 1.74 (m, 2H), 2.16 (s, 3H), 2.89 (m, 2H), 4.14 (m, 2H), 5.74 (m, 1H), 7.03 (d, J=8.8 Hz, 1H), 7.34 (d, J=8.8 Hz, 1H), 7.53 (s, 1H).

2(R),3(S)-Methano-3(3-t-butyl-2-n-pentyl-benzofur-5-yl)-butan-1-ol (Compound 34)

By using the procedure used for the preparation of 2(R),3(S)-methano-3(3-t-butyl-2-ethyl-benzofur-5-yl)-butan-1-ol (Compound 8), 3-(3-t-butyl-2-pentyl-benzofur-5-yl)-but-2(Z)-en-1-ol (Compound 33) was converted into the title compound.

By following the procedure used for the preparation of carnphenoate ester Compound 17, 2(R),3(S)-methano-3(3-t-butyl-2-n-pentyl-benzofur-5-yl)-butan-1-ol (Compound 34), was converted into the camphenoate ester Compound 35, and the major diastereomer was separated by HPLC from the contaminating minor diastereomer.

$^1$H NMR (300 MHz, CDCl$_3$): δ 0.80–0.95 (m, 5H), 0.96 (s, 3H), 1.03 (s, 3H), 1.12 (s, 3H), 1.36 (m, 5H), 1.42 (s, 3H), 1.49 (s, 9H), 1.71 (m, 3H), 1.90 (m, 1H), 1.99 (m, 1H), 2.37 (m, 1H), 2.86 (m, 2H), 3.75 (dd, J=7.6, 11.4 Hz, 1H), 3.97 (dd, J=7.6, 11.4 Hz, 1H), 7.14 (d, J=8.3 Hz, 1H), 7.25 (d, J=8.3 Hz, 1H), 7.59 (s, 1H).

2(R),3(S)-Methano-3(3-t-butyl-2-n-pentyl-benzofur-5-yl)-butan-1-ol (Compound 34)

By following the procedure used for the preparation of 2(R),3(S)-Methano-3(2,3-diethyl-benzofur-5-yl)-butan-1-ol (Compound 16), the camphenoate ester Compound 35 was converted into the title compound.

$^1$H NMR (300 MHz, CDCl$_3$): δ 0.80 (m, 4H), 1.27 (m, 6H), 1.35 (s, 3H), 1.40 (s, 9H), 1.60 (m, 2H), 2.77 (m, 2H), 3.18 (m, 2H), 7.07 (d, J=8.8 Hz, 1H), 7.20 (d, J=8.8 Hz, 1H), 7.55 (s, 1H).

2(R),3(S)-Methano-3-(3-t-butyl-2-n-pentyl-benzofur-5-yl)-butanal (Compound 36)

By following the procedure used for the preparation of 2(R),3(S)-methano-3(3-t-butyl-2-ethyl-benzofur-5-yl)-butanal (Compound 9), 2(R),3 (S)-methano-3(3-t-butyl-2-n-pentyl-benzofur-5-yl)-butan-1-ol (Compound 34) was converted into the title compound.

$^1$H NMR (CDCl$_3$): δ 0.90 (m, 3H), 1.36 (m, 4H), 1.49 (m, 12H), 1.70 (m, 3H), 1.94 (m, 2H), 2.86 (m, 2H), 7.15 (d, J=8.8 Hz, 1H), 7.29 (d, J=8.8 Hz, 1H), 7.63 (s, 1H), 8.44 (d, J=7.1 Hz, 1H).

Ethyl-3-methyl-6(S),7(S)-methano-7-(3-t-butyl-2-n-pentyl-benzofur-5-yl)-octa-2(E),4(E)-dienoate (Compound 37)

By following the procedure used for the preparation of ethyl-3-methyl-6(S),7(S)-methano-7-(3-t-butyl-2-ethyl-benzofur-5-yl)-octa-2(E),4(E)-dienoate (Compound 10), 2(R),3(S)-methano-3-(3-t-butyl-2-n-pentyl-3-iso-propyl-benzofur-5-yl)-butanal (Compound 36) was converted into the title compound.

$^1$H NMR (CDCl$_3$): δ 0.90 (m, 3H), 1.14 (m, 1H), 1.26 (m, 4H), 1.37 (m, 4H), 1.45 (m, 12H), 1.70 (m, 3H), 1.95 (s, 3H), 2.86 (m, 2H), 4.13 (q, J=7.3 Hz, 2H), 5.25 (dd, J=10.0, 15.5 Hz, 1H), 5.64 (s, 1H), 6.24 (d, J=15.5 Hz, 1H), 7.09 (d, J=8.8 Hz, 1H), 7.27 (d, J=8.8 Hz, 1H), 7.54 (s, 1H).

3-Methyl-6(S),7(S)-methano-7-(3-t-butyl-2-n-pentyl-benzofur-5-yl)-octa-2(E),4(E)-dienoic acid (Compound 38)

By following the procedure used for the preparation of 3-methyl-6(S),7(S)-methano-7-(3-t-butyl-2-ethyl-benzofur-5-yl)-octa-2(E),4(E)-dienoic acid (Compound 12), ethyl-3-methyl-6(S),7(S)-methano-7-(3-t-butyl-2-n-pentyl-benzofur-5-yl)-octa-2(E),4(E)-dienoate (Compound 37) was converted into the title compound.

$^1$H NMR (CDCl$_3$): δ 0.90 (m, 3H), 1.15 (m, 1H), 1.27 (m, 1H), 1.36 (m, 4H), 1.45 (m, 12H), 1.70 (m, 3H), 1.94 (s, 3H), 2.86 (m, 2H), 5.30 (dd, J=10.0, 15.5 Hz, 1H), 5.64 (s, 1H), 6.26 (d, J=15.5 Hz, 1H), 7.09 (d, J=8.8 Hz, 1H), 7.25 (d, J=8.8 Hz, 1H), 7.53 (s, 1H).

What is claimed is:
1. A compound of the formula

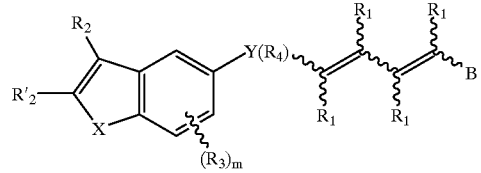

X is O, NR' or S where R' is alkyl of 1 to 6 carbons;

Y is a bivalent cyclopropyl radical optionally substituted with one or two R$_4$ groups, or Y is a bivalent aryl or 5 or 6 membered heteroaryl radical having 1 to 3 heteroatoms selected from N, S and O, said aryl or heteroaryl groups optionally substituted with 1 to 4 R$_4$ groups;

R$_1$ is independently H, alkyl of 1 to 6 carbons, or fluoroalkyl of 1 to 6 carbons;

R$_2$ is alkyl of 1 to 8 carbons, or fluoroalkyl of 1 to 8 carbons;

R'$_2$ is alkyl of 1 to 8 carbons, or fluoroalkyl of 1 to 8 carbons;

R$_3$ is hydrogen, alkyl of 1 to 6 carbons, fluoro substituted alkyl of 1 to 6 carbons, halogen, alkoxy of 1 to 8 carbons, or alkylthio of 1 to 6 carbons; NO$_2$, NH$_2$, NHCO(C$_1$–C$_6$ alkyl, NHCO(C$_1$–C$_6$)alkenyl, NR$_1$H or N(R$_1$)$_2$, benzyloxy or C$_1$–C$_6$alkyl-substituted benzyloxy;

R$_4$ is H or alkyl of 1 to 6 carbons, or fluoro substituted alkyl of 1 to 6 carbons;

m is an integer having the values of 0 to 3, and

B is COOH or a pharmaceutically acceptable salt thereof, COOR$_8$, COOCH$_2$COR$_7$, CONR$_9$R$_{10}$, —CH$_2$OH, CH$_2$OR$_{11}$, CH$_2$OCOR$_{11}$, CHO, CH(OR$_{12}$)$_2$, CH(OR$_{13}$O), —COR$_7$, CR$_7$(OR$_{12}$)$_2$, CR$_7$(OR$_{13}$O), where R$_7$ is an alkyl, cycloalkyl or alkenyl group containing 1 to 5 carbons, R$_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl, hydroxyphenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

2. A compound in accordance with claim 1 where X is O.

3. A compound in accordance with claim 1 where X is S.

4. A compound in accordance with claim 1 where X is NR'.

5. A compound in accordance with claim 4 where X is NH'.

6. A compound in accordance with claim 1 where Y is a bivalent cyclopropyl radical.

7. A compound in accordance with claim 1 where Y is a bivalent phenyl radical.

8. A compound in accordance with claim 1 where Y is a bivalent pyridine radical.

9. A compound in accordance with claim 1 where Y is a bivalent furan or thiophene radical.

10. A compound in accordance with claim 1 where B is COOH or a pharmaceutically acceptable salt thereof, or $COOR_8$.

11. A compound of the formula

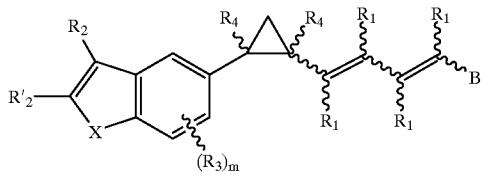

where $R_1$ is independently H, alkyl of 1 to 6 carbons, or fluoroalkyl of 1 to 6 carbons;

$R_2$ is alkyl of 1 to 8 carbons, or fluoroalkyl of 1 to 8 carbons;

$R'_2$ is alkyl of 1 to 8 carbons, or fluoroalkyl of 1 to 8 carbons;

$R_3$ is hydrogen, alkyl of 1 to 6 carbons, fluoro substituted alkyl of 1 to 6 carbons, halogen, alkoxy of 1 to 6 carbons, or alkylthio of 1 to 6 carbons; $NO_2$, $NH_2$, $NHCO(C_1–C_6$ alkyl), $NHCO(C_1–C_6)$alkenyl, $NR_1H$ or $N(R_1)_2$;

$R_4$ is H or alkyl of 1 to 6 carbons, or fluoro substituted alkyl of 1 to 6 carbons;

m is an integer having the values of 0 to 3, and

B is COOH or a pharmaceutically acceptable salt thereof, $COOR_8$, $COOCH_2COR_7$, $CONR_9R_{10}$, $—CH_2OH$, $CH_2OR_{11}$, $CH_2OCOR_{11}$, $CHO$, $CH(OR_{12})_2$, $CH(OR_{13}O)$, $—COR_7$, $CR_7(OR_{12})_2$, $CR_7(OR_{13}O)$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl, hydroxyphenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

12. A compound in accordance with claim 11 where B is COOH or a pharmaceutically acceptable salt thereof, or $COOR_8$.

13. A compound in accordance with claim 11 $R_1$ is H or methyl.

14. A compound in accordance with claim 11 where $R_4$ is H or methyl.

15. A compound in accordance with claim 11 where $R_2$ and $R'_2$ are alkyl of 1 to 6 carbons.

16. A compound in accordance with claim 11 where at least one of the $R_2$ and $R'_2$ groups is branch-chained alkyl.

17. A compound in accordance with claim 16 where at least one of the $R_2$ and $R'_2$ groups is branch-chained alkyl and the other is normal-alkyl.

18. A compound in accordance with claim 16 where the $R_2$ and $R'_2$ groups both are branch-chained alkyl.

19. A compound of the formula

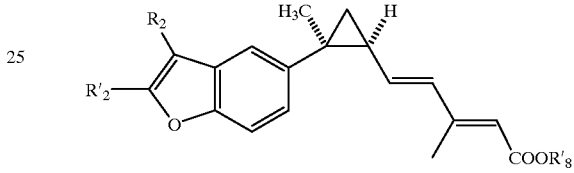

where $R_2$ is alkyl of 1 to 6 carbons;

$R'_2$ is alkyl of 1 to 6 carbons, and $R'_8$ is COOH or a pharmaceutically acceptable salt thereof, or $COOR_8$ where $R_8$ is alkyl of 1 to 6 carbons.

20. A compound in accordance with claim 19 where $R_2$ is branch-chained alkyl.

21. A compound in accordance with claim 19 where $R'_2$ is branch-chained alkyl.

22. A compound in accordance with claim 19 where $R_2$ and $R'_2$ are both branch-chained alkyl.

23. A compound in accordance with claim 19 where $R_2$ is t-butyl and $R'_2$ is ethyl.

24. A compound in accordance with claim 23 where $R'_8$ is H or ethyl.

25. A compound in accordance with claim 19 where $R_2$ is ethyl and $R'_2$ is ethyl.

26. A compound in accordance with claim 25 where $R'_8$ is H or ethyl.

27. A compound in accordance with claim 19 where $R_2$ is i-propyl and $R'_2$ is ethyl.

28. A compound in accordance with claim 23 where $R'_8$ is H or ethyl.

29. A compound in accordance with claim 19 where $R_2$ is t-butyl and $R'_2$ is n-pentyl.

30. A compound in accordance with claim 29 where $R'_8$ is H or ethyl.

* * * * *

UNITED STATES PATENT AND TRADEMARK OFFICE
CERTIFICATE OF CORRECTION

PATENT NO. : 6,388,105 B1
DATED : May 14, 2002
INVENTOR(S) : Vuligonda et al.

It is certified that error appears in the above-identified patent and that said Letters Patent is hereby corrected as shown below:

Title page,
Item [56], US PATENT DOCUMENTS, insert
-- 5,324,840  6/1994   Chandraratna
   5,344,959  9/1994   Chandraratna
   5,455,265  10/1995  Chandraratna
   5,466,861  11/1995  Dawson, et al.
   5,675,033  10/1997  Vuligonda, et al.
   5,728,846  3/1998   Vuligonda, et al.
   5,877,207  3/1999   Klein, et al.
   5,917,082  6/1999   Vuligonda, et al.
   6,034,110  3/2000   Nagpal, et al.
   6,048,873  4/2000   Vasudevan, et al.
   6,093,838  7/2000   Vasudevan, et al.
   6,172,115  6/2001   Chadraratna   --.
-- FOREIGN PATENT DOCUMENTS
   WO  93/11755  6/1993
   WO  93/21162  4/1993
   WO  96/05165  2/1996
   EP  0098591   7/1983

OTHER DOCUMENTS
      Dawson and William H. Okamura, Chemistry and Biology of Synthetic Retinoids, published by CRC Press Inc., 1990, pages 334-335, 354 and 324-356
*Janusz et al.* J. Med. Chem. 1998 *41* 1124-1137
*Iida et al.* Tetrahedron Letters 35, 1982 p 3591-3594
*Vuligonda et al.* Biorg. Med. Lett. *6*(2) 213-8, 1996
*J. Amer. Chem. Soc.* 1998, *120*, 11943-11952
*J. Org. Chem.* 1974, Volume 39 pages 821-825  --.

Column 1,
Line 43, insert -- , -- after "system".
Line 46, "can-be" should be -- can be --.

Column 2,
Line 51, delete "." after "Having".

Column 3,
Line 50, "or a group of 5 to 10 phenyl" should be -- or a cycloalkyl group of 5 to 10 carbons, or $R_8$ is phenyl --.

UNITED STATES PATENT AND TRADEMARK OFFICE
CERTIFICATE OF CORRECTION

PATENT NO. : 6,388,105 B1
DATED : May 14, 2002
INVENTOR(S) : Vuligonda et al.

It is certified that error appears in the above-identified patent and that said Letters Patent is hereby corrected as shown below:

Column 5,
Line 17, " RXγ" should be -- RXRγ --.

Column 7,
Line 27, "dermatoses'" should be -- dermatoses; --.

Column 9,
Line 18, "The compounds of..." should begin a new paragraph.
Line 37, "ot-bromo" should be -- α-bromo --.
Line 47, "dilhydiobenzothiophene" should be -- dihydrobenzothiophene --.

Column 12,
Line 41, "behzofuranyl" should be -- benzofuranyl --.

Column 15,
Line 21, "Horner Emmons..." should be on the same line as "This latter".

Column 16,
Lines 49 and 66, "C." should be -- C --.

Column 17,
Lines 5, 27, 47 and 60, "C." should be -- C --.
Line 31, both occurrences of "C." should be -- C --.

Column 18,
Line 5, the first occurrence of "C." should be -- C --.
Line 6, "diluted-" should be -- diluted --.
Line 38, "C." should be -- C --.

Column 19,
Lines 2, 17, 19 and 58, "C." should be -- C --.
Line 55, "$CH_2Cl2$" should be -- $CH_2Cl_2$ --.

Column 23,
Lines 2 and 6, "C." should be -- C --.
Line 27, "carnphenoate" should be -- camphenoate --.

UNITED STATES PATENT AND TRADEMARK OFFICE
CERTIFICATE OF CORRECTION

PATENT NO. : 6,388,105 B1
DATED : May 14, 2002
INVENTOR(S) : Vuligonda et al.

It is certified that error appears in the above-identified patent and that said Letters Patent is hereby corrected as shown below:

Column 25,
Line 31,

"
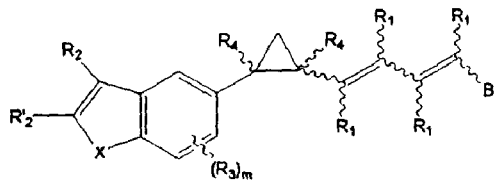
"

should be

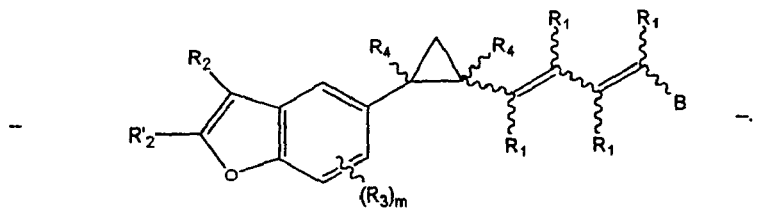

Signed and Sealed this

Twenty-eighth Day of January, 2003

JAMES E. ROGAN
*Director of the United States Patent and Trademark Office*